United States Patent
Suzuki et al.

(10) Patent No.: US 7,345,008 B1
(45) Date of Patent: Mar. 18, 2008

(54) FRESHNESS-KEEPING AGENTS FOR PLANTS

(75) Inventors: Tadayuki Suzuki, Wakayama (JP); Masatoshi Kamei, Wakayama (JP); Masaharu Hayashi, Wakayama (JP); Kazuhiko Kurita, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/744,678

(22) PCT Filed: Jul. 29, 1999

(86) PCT No.: PCT/JP99/04080

§ 371 (c)(1),
(2), (4) Date: Apr. 10, 2001

(87) PCT Pub. No.: WO00/05946

PCT Pub. Date: Feb. 10, 2000

(30) Foreign Application Priority Data

Jul. 29, 1998 (JP) .................. 10-214105
Jul. 29, 1998 (JP) .................. 10-214106
Dec. 9, 1998 (JP) .................. 10-349965

(51) Int. Cl.
*A01N 3/02* (2006.01)
(52) U.S. Cl. .................................................. 504/114
(58) Field of Classification Search ............... 504/116, 504/114
See application file for complete search history.

(56) References Cited

U.S. PATENT DOCUMENTS

| | | | | |
|---|---|---|---|---|
| 3,929,448 | A | * 12/1975 | Brantley | 504/115 |
| 5,635,443 | A | 6/1997 | Lesenko | |
| 5,747,416 | A | * 5/1998 | McArdle | 504/115 |
| 5,958,104 | A | * 9/1999 | Nonomura et al. | 71/11 |

FOREIGN PATENT DOCUMENTS

| | | | |
|---|---|---|---|
| EP | 0 557 946 A1 | | 9/1993 |
| JP | A49120781 | | 11/1974 |
| JP | A5081856 | | 7/1975 |
| JP | 51110032 | * | 9/1976 |
| JP | 54020010 | * | 2/1979 |
| JP | 55083707 | * | 6/1980 |
| JP | 59189185 | * | 10/1984 |
| JP | 63033310 | * | 2/1988 |
| JP | 02209801 | * | 8/1990 |
| JP | 06227904 | * | 8/1994 |
| JP | A6227904 | | 8/1994 |
| JP | 06336401 | * | 12/1994 |
| JP | A6336401 | | 12/1994 |
| JP | A7187902 | | 7/1995 |
| JP | 07291856 | * | 11/1995 |
| JP | A8509375 | | 10/1996 |
| JP | A10501553 | | 2/1998 |
| WO | 9424857 | * | 11/1994 |
| WO | 9534199 | | 12/1995 |

OTHER PUBLICATIONS

Database WPI, Section Ch. Week 199508, Derwent Publications Ltd., London GB; An 1995-057268, XP002360777.

* cited by examiner

*Primary Examiner*—Alton Pryor
(74) *Attorney, Agent, or Firm*—Birch, Stewart, Kolasch & Birch, LLP

(57) ABSTRACT

The present invention provides a freshness-keeping agent for plants, such as a harvested plant, demonstrating an effect of keeping the freshness without selecting a type among various plants such as a harvested plant and also having a high safety. That is, the present invention provides a freshness-keeping agent for plants, such as a harvested plant, comprising a sugar derivative- or sugar alcohol derivative-based surfactant (A) and at least one selected from the group consisting of a sugar (B), a plant hormone (C), an aging inhibitor (D), an aggregating agent for colloidal particles (E) and a germicide, fungicide and preservative (F), preferably in a specific ratio by weight.

26 Claims, No Drawings

FRESHNESS-KEEPING AGENTS FOR PLANTS

This application is the national phase under 35 U.S.C. § 371 of PCT International Application No. PCT/JP99/04080 which has an International filing date of Jul. 29, 1999, which designated the United States of America.

TECHNICAL FIELD

The present invention relates to a freshness-keeping agent for plants such as a harvested plant, particularly a cut flower, a vegetable etc.

BACKGROUND ART

The conventional methods of prolonging a life of a cut flower and maintaining its freshness include a method of cutting the flower in fresh water; a method of crushing or burning the cut surface to improve preservation in water; a method of adding a nutrient source such as sugars to water; and a method of adding a preservative or germicide for preventing multiplication of a microorganism or fungus, an aggregating and precipitating agent for colloidal particles, such as aluminum sulfate, for the purpose of aggregating colloidal particles such as a substance leaked from the plant or a metabolite occurring upon generation of microorganisms, or chemicals such as silver thiosulfate for suppressing biosynthesis of ethylene; etc. That is, various techniques have been devised. Then, various agents for prolonging the life of the cut flower are commercially available.

However, the publicly known methods described above suffer from the various problems that their effect on keeping the freshness of the cut flower and vegetable is not satisfactory, that the limited type of the cut flower and vegetable is demonstrated to be effected, their procedure to use themselves is complicated, and the safety on the environment and humans and domestic animals is worried about.

Further, JP-A 6-336401 discloses a technique wherein a perfume glycoside enhances an aroma of a cut flower.

On the other hand, JP-A 6-227904 and JP-A 7-330502 only disclose techniques of keeping a freshness of a cut flower or the like by use of trehalose or a salt thereof but don't disclose a surfactant etc.

DISCLOSURE OF INVENTION

In view of the problems described above, the object of the present invention is to provide a freshness-keeping agent for plants demonstrating an effect of keeping the freshness without selecting a type among various plants and also having a high safety. It is preferably suitable for a harvested plant, in particular. Further, the freshness of a living plant not harvested is also improved by the present invention. The living plant may be a rooted plant, for example. The harvested plant may be a cut flower, a vegetable, a cut leave or a tree or branch with a flower. In the present invention, the freshness-keeping agent for plants is preferably suitably used for keeping the freshness of the cut flower and vegetables, in particular.

The present invention provides a freshness-keeping composition for plants comprising at least one surfactant selected from a sugar derivative-based surfactant and sugar alcohol derivative-based surfactant (A) and at least one selected from the group consisting of sugar (B), a plant hormone (C), an aging inhibitor (D), an aggregating agent for colloidal particles (E), and a germicide, fungicide and preservative (F).

It is preferable in the present invention that a hydrophobic group is bound via a glycoside, ester or amide linkage to the sugar or sugar alcohol in the component (A).

It is preferable in the present invention that the ratio of (A)/(B) by weight is 0.00001 to 2.0; the ratio of (A)/(C) by weight is 0.0002 to 10000; the ratio of (D)/(A) by weight is 0.0002 to 1000; the ratio of (A)/(E) by weight is 0.0002 to 1000; or the ratio of (A)/(F) by weight is 0.00001 to 200.

The present invention also provides a method of preserving a plant with keeping the freshness thereof, which comprises applying an effective amount of the composition described above to the plant.

Further, the present invention provides use of the composition described above for preserving a plant with keeping the freshness thereof.

Preferably, the sugar (B) is at least one member selected from a monosaccharide, oligosaccharide and polysaccharide. The plant hormone (C) is preferably at least one member selected from auxins, cytokinins, gibberellins and brassinosteroids.

On the other hand, preferably, the aging inhibitor (D) has at least an ability to impede biosynthesis of ethylene or to suppress an action of ethylene.

The aggregating agent for colloidal particles (E) has at least an action of aggregating or precipitating colloidal particles exerting an adverse action on plants.

Otherwise, preferably, the germicide, fungicide or preservative (F) has at least a germicidal action, a fungicidal action, an antibacterial action or a bacteriostatic action.

MODES FOR CARRYING OUT THE INVENTION

Insofar as the sugar derivative-based surfactant or sugar alcohol derivative-based surfactant (A) used in the present invention has a surfactant activity with a sugar or sugar alcohol skeleton in a molecule, a type thereof is not limited and any one thereof may be used.

The surfactant with a structure having a hydrophobic group bound via an ester linkage to the sugar or sugar alcohol thereof includes a sorbitan fatty acid ester, a polyoxyalkylene sorbitan fatty acid ester, a sucrose fatty acid ester, a sorbitol fatty acid ester, a polyoxyalkylene sorbitol fatty acid ester, a polyglycerol, a polyglycerol fatty acid ester, a glycerol fatty acid ester and a polyoxyalkylene glycerol fatty acid ester.

The surfactant with a structure having a hydrophobic group bound via a glycoside linkage to the sugar or sugar alcohol thereof includes an alkyl glycoside, an alkyl polyglycoside, a polyoxyalkylene alkyl (poly)glycoside, an alkyl (poly)glycoside sulfate comprising an alkyl (poly)glucoside sulfated therein, a phosphated alkyl (poly)glycoside, a glyceryl etherified alkyl (poly)glycoside, a sulfosuccinated alkyl (poly)glycoside, a glyceryl-esterified alkyl (poly)glycoside, a carboxy-alkylated alkyl (poly)glycoside, a cationic alkyl (poly)glycoside, and a betaine alkyl (poly)glycoside.

As the component (A), it is possible to use a compound with a structure having a hydrophobic group bound via an amide linkage to the sugar or sugar alcohol thereof, for example a sugar-based fatty acid amide such as a fatty acid amide of glucose or fructose. Further, it is also possible to use a compound with a structure having a hydrophobic group bound via an amide linkage to the amino group-containing sugar or sugar alcohol thereof, for example a sugar-based fatty acid amide such as a fatty acid amide of N-methylglucamine.

As the sugar-based fatty acid amide, a compound represented by the formula (1):

wherein $R^1$ is a $C_{5-17}$ linear or branched alkyl, alkenyl or alkylphenyl group, $R^2$ is hydrogen, a $C_{1-18}$ linear or branched alkyl or alkenyl group, $-(CH_2CH(R^3)O)_c-H$ (whereupon $R^3$ is hydrogen or a methyl group and c is a number selected from 0 to 10), $-CH_2CH_2OH$, $-CH_2CH(OH)CH_3$ or $-CH_2CH_2CH_2OH$, and $X^1$ is a polyhydroxy alkyl group comprising a $C_{4-30}$ sugar residue can be preferably used.

In consideration of $R^1$ in the formula (1) including a $C_{5-17}$ linear or branched alkyl, alkenyl or alkylphenyl group, $R^1CO$ can include a group derived from capric acid, caprylic acid, lauric acid, myristic acid, palmitic acid, stearic acid and isostearic acid, and preferably a group derived from capric acid and lauric acid in particular.

Specific example of $R^2$ may be hydrogen, methyl group, ethyl group, n-propyl group, isopropyl group, n-butyl group, t-butyl group, n-hexyl group, octyl group, 2-ethyl hexyl group, decyl group, dodecyl group, stearyl group, isostearyl group, or a polyethylene glycol or polypropylene glycol group having a degree of polymerization of 2 to 10, 2-hydroxyethyl group, 2-hydroxypropyl group, 3-hydroxypropyl group or the like. Among them, hydrogen, methyl group, ethyl group, 2-hydroxyethyl group, 2-hydroxypropyl group and 3-hydroxypropyl group can be mentioned as preferable examples.

Then, $X^1$ of a polyhydroxy alkyl group comprising a $C_{4-30}$ sugar residue includes a $C_{4-7}$ polyhydroxy alkyl group bound via a glycoside linkage to a mono-, di- or oligosaccharide group.

The component (A) is preferably a sorbitan fatty acid ester, an alkyl polyglycoside or a sucrose fatty acid ester.

The sorbitan fatty acid ester is preferably a compound having a higher content of monoesters and having HLB (hydrophilic Lypophilic Balance) in the range of 3 to 10. Further, the acyl group constituting its hydrophobic group is preferably a $C_{8-18}$ group which may be any one of saturated, unsaturated, linear and branched groups.

The alkyl polyglycoside has preferably an average degree of sugar condensation of 1.1 to 5.0 and more preferably 1.1 to 2.0. The sugar skeleton is preferably a glucose skeleton with an average degree of sugar condensation of 1.1 to 2.0. The hydrophobic group is preferably a $C_{8-18}$ group and more preferably a $C_{8-14}$ group, which may be any one of saturated, unsaturated, linear and branched groups.

The sucrose fatty acid ester comprises a mixture of mono-, di-, tri- and polyester (tetraester or higher ester). It is preferable that the mixture has a higher content of monoesters and diesters, that a lower content of polyesters and that HLB is within the range of 4 to 18. The acyl group constituting its hydrophobic group is preferably a $C_{8-18}$ group which may be any one of saturated, unsaturated, linear and branched groups.

At least one sugar (B) used in the present invention and selected from monosaccharides, oligosaccharides and polysaccharides is not limited insofar as it is a sugar being able to become a nutrient source or energy source for a cut flower, vegetables etc. For example, the sugar (B) includes monosaccharides such as glucose, xylose, arabinose, ribose, galactose, fructose, mannose, rhamnose, inositol, sorbitol, mannitol, xylitol, glycerol, erythritol, glucosamine and galactosamine; oligosaccharides such as sucrose, trehalose, trehalose, maltose, cellobiose, palatinose, lactose, raffinose, cyclodextrin, xylo-oligosaccharide, fructo-oligosaccharide, galacto-oligosaccharide, malto-oligosaccharide, inulo-oligosaccharide and lactosucrose; and polysaccharides such as agarose, amylose, glycogen, cellulose, dextrin, inulin, mannan and chitin. One or more sugars described above, preferably two or more sugars, are incorporated into the freshness-keeping agent for plants.

The plant hormone (C) includes natural or synthetic auxins such as IAA (indole-3-acetic acid), 2,4-dichlorophenoxyacetic acid, 2,6-dichlorobenzoic acid and naphthalene acetic acid, natural or synthetic cytokinins such as zeatin, kinetin, 4-benzyl aminobenzimidazole and benzyl adenine, and gibberellins, and brassinosteroids such as brassinolide and castasterone.

The component (D) having the action of impeding the formation or action of ethylene, thus inhibiting the aging of a plant, includes AVG (aminoethoxyvinyl glycine), AOA (aminooxyacetate hemihydrochloride), PACME (isopropyridine-aminooxyacetate-2-mehtoxy-2-oxoethyl ester), STS (silver thiosulfate or silver thiosulfate complex salt), AIB (aminoisobutyric acid), DPSS (1,1-dimethyl-4-(phenyl sulfonyl) semicarbazide), PPOH (cispropenyl phosphonic acid), STB (sodium tetraborate), allocoronamic acid, aminotriazole, phenanthroline, DACP (diazocyclopentadiene), AITC (isothiocyanic acid allyl ester), NBD (2,5-norbornadiene), MCP (1-methyl cyclopropene), and ethionine. That is, the aging inhibitor (D) used in the present invention is not limited insofar as it is a component having an ability to impede biosynthesis of ethylene or an ability to suppress the action of ethylene, thus preventing the aging of a plant. Further examples thereof include a silver compound such as silver chloride, silver chelated by amino acid, silver benzoate, silver lactate, silver nitrate, silver chelated by zeolite, silver chelated by silica gel, and silver chelated by hydroxyapatite.

For the purpose of aggregating or precipitating colloidal particles exerting an adverse action on a plant, such as a substance leaked from the plant and a metabolite occurring upon generation of microorganisms, it is also possible to incorporate, as the component (E), an aluminum compound such as aluminum sulfate, aluminum potassium sulfate, sodium aluminate, polyaluminum chloride, ammonium alum, aluminum lactate and aluminum silicate; calcium chloride; a combination of calcium chloride and phosphoric acid; a polymer aggregate such as a neutralized salt of dimethyl aminoethyl methacrylate, a product of Mannich reaction of polyacrylamide, a product of Hofmann rearrangement reaction of polyacrylamide, a condensate of alkylamine and epichlorohydrin, polyvinyl amine, chitosan etc.

For example, at least one of germicide, fungicide and preservative (F) having a germicidal action, a fungicidal action, an antibacterial action or a bacteriostatic action can be incorporated. Specifically, it may be sodium hypochlorite, copper sulfate, 8-hydroxyquinoline, ethanol, isopropanol, methyl (ethyl, propyl or butyl) p-hydroxybenzoate, Proxel (tradename, Nagase Chemicals Ltd.), Bronopol (Bromonitropropanediol) (trade name, Nagase & Co., Ltd.) or a cationic surfactant. The cationic surfactant includes an alkyl trimethyl ammonium chloride, a dialkyl dimethyl ammonium chloride, benzalkonium chloride, and a polyoxyethylene monoalkyl monomethyl ammonium chloride.

Further, the ratio by weight of the component (A) to the component (B), namely (A)/(B), is preferably in the range of 0.00001 to 2.0, more preferably 0.0001 to 1.0, and most preferably 0.0002 to 0.02.

Further, the ratio by weight of the component (A) to the component (C), namely (A)/(C), is preferably in the range of 0.0002 to 10000, more preferably 0.001 to 1000, and most preferably 0.1 to 100.

Further, the ratio by weight of the component (D) to the component (A), namely (D)/(A), is preferably in the range of 0.0002 to 1000, more preferably 0.001 to 50, and most preferably 0.01 to 10.

Further, the ratio by weight of the component (A) to the component (E), namely (A)/(E), is preferably in the range of 0.0002 to 1000, more preferably 0.0002 to 20, most preferably 0.001 to 10, and particularly most preferably 0.002 to 2.

Further, the ratio by weight of the component (A) to the component (F), namely (A)/(F), is preferably in the range of 0.00001 to 200, more preferably 0.0001 to 100, and most preferably 0.01 to 50.

The freshness-keeping agent for plants of the present invention only comprising the component (A) and at least one selected from the components (B), (C), (D), (E) and (F) can be expected to exhibit its satisfactory effect, but may be incorporated as necessary with a component used in a conventional method of keeping the freshness or used in an agent having a life-prolonging effect of a cut flower or vegetable, for example with a commercial agent for prolonging the life of the cut flower.

Further, an amino acid or inorganic nutrient being able to be a nutrient source for plants may be added.

Further, the freshness-keeping agent for plants of the present invention may be incorporated with one or more other surfactants. The surfactants used in the present invention are as follows.

As the nonionic surfactant, there may be a polyoxyalkylene fatty acid ester, a resinate, a polyoxyalkylene resinate, a polyoxyalkylene alkyl ether, a polyoxyalkylene alkyl phenyl ether, or a silicone-based surfactant.

As the anionic surfactant, there may be a surfactant based on carboxylic acid, sulfonic acid, sulfate or phosphate.

The carboxylic acid-based surfactant may be a $C_{6-30}$ fatty acid or a salt thereof, a polyvalent carboxylic acid or a salt thereof, a polyoxyalkylene alkyl ether carboxylic acid or a salt thereof, a polyoxyalkylene alkyl amide ether carboxylic acid or a salt thereof, rhodinic acid or a salt thereof, a dimer acid or a salt thereof, a polymer acid or a salt thereof, or a toll oil fatty acid or a salt thereof.

The sulfonic acid-based surfactant may be an alkyl benzene sulfonic acid or a salt thereof, an alkyl sulfonic acid or a salt thereof, an alkyl naphthalene sulfonic acid or a salt thereof, naphthalene sulfonic acid or a salt thereof, diphenyl ether sulfonic acid or a salt thereof, a condensate of an alkyl naphthalene sulfonic acid or a salt thereof, or a condensate of naphthalene sulfonic acid or a salt thereof, for instance.

The sulfate-based surfactant may be an alkyl sulfate or a salt thereof, a polyoxyalkylene alkyl sulfate or a salt thereof, a polyoxyalkylene alkyl phenyl ether sulfuric acid or a salt thereof, a tristyrenated phenol sulfate or salts thereof, or a polyoxyalkylene distyrenated phenol sulfate or a salt thereof, for instance.

The phosphate-based surfactant may be an alkyl phosphate or a salt thereof, an alkyl phenyl phosphate or a salt thereof, a polyoxyalkylene alkyl phosphate or a salt thereof, or a polyoxyalkylene alkyl phenyl phosphate or a salt thereof, for instance.

The salt of these compounds may be a metal salt (Na, K, Ca, Mg, Zn etc.), ammonium salt, an alkanol amine salt, or an aliphatic amine salt, for instance.

As the amphoteric surfactant, there may be a surfactant based on amino acid, betaine, imidazoline, or amine oxide.

The amino acid-based surfactant may be an acyl amino acid salt, an acyl sarcosinate, an acryloyl methyl aminopropionate, an alkyl aminopropionate, or an acyl amide ethyl hydroxyethyl methyl carboxylate, for instance.

The betaine-based surfactant may be an alkyl dimethyl betaine, an alkyl hydroxyethyl betaine, an acyl amide propyl hydroxypropyl ammonia sulfobetaine, an acyl amide propyl hydroxypropyl ammonia sulfobetaine, or a ricinoleic acid amide propyl dimethyl carboxymethyl ammonia betaine.

The imidazoline-based surfactant may be an alkyl carboxymethyl hydroxyethyl imidazolinium betaine or an alkyl ethoxy carboxymethyl imidazolium betaine.

The amine oxide-based surfactant may be an alkyl dimethyl amine oxide, an alkyl diethanol amine oxide, or an alkyl amide propyl amine oxide.

The freshness-keeping agent for plants of the present invention may be made as a powdery preparation comprising the sugar derivative- or sugar alcohol derivative-based surfactant (A) and at least one selected from the sugar (B), the plant hormone (C), the aging inhibitor (D), the aggregating agent for colloidal particles (E) and the bactericide, fungicide and preservative (F), as a concentrated aqueous liquid preparation comprising the component (A) and at least one selected from the components (B), (C), (D), (E) and (F) at high concentrations, or as an aqueous liquid preparation used as such.

When the powdery preparation or the concentrated liquid preparation is prepared, these are incorporated such that, to use themselves mixed with water, the component (A) in an amount of 0.0001 to 0.1% by weight, especially 0.0005 to 0.05% by weight, and particularly 0.001 to 0.01% by weight and the component (B) in an amount of 0.05 to 10% by weight, particularly 0.5 to 5% by weight; the component (C) in an amount of 0.00001 to 0.5% by weight, particularly 0.0001 to 0.01% by weight; the component (D) in an amount of 0.0001 to 0.5% by weight and particularly 0.001 to 0.1% by weight; the component (E) in an amount of 0.0001 to 0.5% by weight, particularly 0.001 to 0.1% by weight; or the component (F) in an amount of 0.0001 to 0.5% by weight, particularly 0.0005 to 0.1% by weight. Although there may be at least one of the components (B), (C), (D), (E) and (F), two to five selected therefrom may be incorporated. Here, the amount of each of the components is preferably within the range described above. If the aqueous liquid preparation used as such is prepared, each of the components is dissolved or dispersed in water at the concentration described above.

The freshness-keeping agent for plants of the present invention is also effectively added to a freshness-keeping agent or life-prolonging agent for plants being conventionally used and commercially available. Concerning in a method for adding it, the freshness-keeping agent for plants of the present invention can be added in the form of aqueous solution or powder.

The method of using the freshness-keeping agent for plants of the present invention includes a method of immersing the cut part (cut surface) or the whole of a flower or vegetable in an aqueous solution of the freshness-keeping agent for plants of the present invention, a method of spraying an aqueous solution of the freshness-keeping agent for plants of the present invention to a cut flower or vegetable, and a method of allowing an aqueous solution of the freshness-keeping agent for plants of the present invention to be absorbed into a suitable absorber such as a nonwoven fabric, fibers, a paper article, a foam of urethane or phenol resin, cotton, and a water-absorbing polymer and then wrapping or sticking a cut flower or vegetable in the absorber.

The cut flower, vegetable and so on to which the freshness-keeping agent for plants of the present invention can be applied are not limited. However, for example, the cut flower includes rose, carnation, lily, orchid, babies'-breath, Turkish balloon flower, Transvaal daisy, chrysanthemum, solidaster lutens, cherry, peach, Chinese black pine, lilly-of-the-incas, hydrangea, delphinium, statice and stock. The vegetable includes, for example, a leaf vegetable such as Chinese cabbage, cabbage, spinach, lettuce, komatsuna (a kind of Chinese cabbage) and crown daisy, a fruit vegetable such as cucumber, tomato, eggplant, green pepper and strawberry, and a root vegetable such as radish, burdock and carrot.

INDUSTRIAL APPLICABILITY

According to the present invention, a freshness-keeping agent exerting a freshness-keeping effect on a variable harvested plants and having a high safety can be obtained.

EXAMPLES

Preparation of a Freshness-Keeping Agent for Plants

Example 1

The freshness-keeping agents having the compositions shown in Table 1 were prepared (Inventive products 1 to 22 and Comparative products 1 to 11). In Table 1, the balance is tap water.

TABLE 1

| No. | Sugar (B) | Sugar derivative-based or sugar alcohol derivative-based surfactant (A) |
|---|---|---|
| Inventive product | | |
| 1 | Glucose 2.0% | Decyl polyglucoside 100 ppm |
| 2 | Sorbitol 0.1% | Decyl polyglucoside 100 ppm |
| 3 | Lactosucrose 5.0% | Decyl polyglucoside 100 ppm |
| 4 | Galactose 0.5% + glucose 0.5% | Decyl polyglucoside 100 ppm |
| 5 | Fructose 1.0% + glucose 1.0% | Decyl polyglucoside 100 ppm |
| 6 | Sucrose 0.5% | Decyl polyglucoside 100 ppm |
| 7 | Glucose 2.0% | Sucrose fatty acid ester 100 ppm |
| 8 | Sorbitol 0.1% | Sucrose fatty acid ester 100 ppm |
| 9 | Lactosucrose 5.0% | Sucrose fatty acid ester 100 ppm |
| 10 | Galactose 0.5% + glucose 0.5% | Sucrose fatty acid ester 100 ppm |
| 11 | Fructose 1.0% + glucose 1.0% | Sucrose fatty acid ester 100 ppm |
| 12 | Sucrose 0.5% | Sucrose fatty acid ester 100 ppm |
| 13 | Trehalose 1.0% | Sucrose fatty acid ester 100 ppm |
| 14 | Glucose 2.0% | Sorbitan fatty acid ester 100 ppm |
| 15 | Sorbitol 0.1% | Sorbitan fatty acid ester 100 ppm |
| 16 | Lactosucrose 5.0% | Sorbitan fatty acid ester 100 ppm |
| 17 | Galactose 0.5% + glucose 0.5% | Sorbitan fatty acid ester 100 ppm |
| 18 | Fructose 1.0% + glucose 1.0% | Sorbitan fatty acid ester 100 ppm |
| 19 | Sucrose 0.5% | Sorbitan fatty acid ester 100 ppm |
| 20 | Glucose 2.0% | Sugar-based fatty acid amide 100 ppm |
| 21 | Lactosucrose 5.0% | Sugar-based fatty acid amide 100 ppm |
| 22 | Fructose 1.0% + glucose 1.0% | Sugar-based fatty acid amide 100 ppm |

TABLE 1-continued

| No. | Sugar (B) | Sugar derivative-based or sugar alcohol derivative-based surfactant (A) |
|---|---|---|
| Comparative product | | |
| 1 | Tap water | — |
| 2 | Glucose 2.0% | — |
| 3 | Sorbitol 0.1% | — |
| 4 | Lactosucrose 5.0% | — |
| 5 | Galactose 0.5% + glucose 0.5% | — |
| 6 | Fructose 1.0% + glucose 1.0% | — |
| 7 | Sucrose 0.5% | — |
| 8 | Chrysal 2% (diluted to 50-fold) | — |
| 9 | Repeat 2% (diluted to 50-fold) | — |
| 10 | Trehalose 1.0% | — |
| 11 | — | Decyl polyglucoside 100 ppm |

(Notes)

Decyl polypolyglucoside: MYDOL 10 (degree of condensation of 1.3, the number of carbon atoms in the alkyl is 9 to 11), produced by Kao Corp.

Sucrose fatty acid ester: DK ester S-L18A (fatty acid: lauric acid), produced by Dai-ichi Kogyo Seiyaku Co., Ltd., monoester/di, triester=70/30.

Sorbitan fatty acid ester: RHEODOL SP-L10 (fatty acid: coconut oil fatty acid), produced by Kao Corp., HLB=8.6

Sugar-based fatty acid amide:

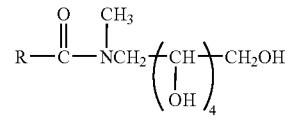

(R—CO: lauroyl)

Chrysal: a commercial freshness-keeping agent for plants, Chrysal Japan

Repeat: a commercial freshness-keeping agent for plants, Taisho Pharmaceutical Co., Ltd.

<Freshness-Keeping Test on Cut Flowers>

The freshness-keeping agents of Inventive products 1 to 22 and Comparative products 1 to 11 were used and examined in a freshness keeping test on commercial cut flowers [chrysanthemum (form: Beniougi), carnation (form: Juliet) and rose (form: Valerie)]. As the cut flowers, those having most similar growth conditions and freshness conditions with the possibility were selected and their stems were cut with sharp scissors in water to use themselves. The cut flowers were placed in 200 ml of the freshness-keeping agent and cultivated under the conditions of a temperature of 23° C., a humidity of 60% and an irradiation of 5000 lux. The keeping of freshness was evaluated visually. The number of days having elapsed until the cut flowers became unappreciable due to withering of flower petals, generation of bent necks, weathering of stems and leaves, etc., was regarded as the number of days for the flowers being preserved. The results are shown in Table 2. As compared with Comparative products, Inventive products were confirmed to have the effect for the flowers being preserved in all test systems, and the freshness-keeping effect of the sugar derivative- or sugar alcohol derivative-based surfactant (A) was thus recognized.

TABLE 2

| No. | the number of days for the flowers being preserved | | |
|---|---|---|---|
| | chrysanthemum | carnation | rose |
| Inventive product | | | |
| 1 | 10 | 10 | 9 |
| 2 | 9 | 9 | 8 |
| 3 | 8 | 8 | 7 |
| 4 | 9 | 9 | 8 |
| 5 | 12 | 12 | 10 |
| 6 | 10 | 9 | 8 |
| 7 | 12 | 11 | 10 |
| 8 | 10 | 10 | 8 |
| 9 | 9 | 9 | 8 |
| 10 | 10 | 10 | 9 |
| 11 | 13 | 12 | 12 |
| 12 | 10 | 11 | 10 |
| 13 | 10 | 9 | 8 |
| 14 | 11 | 10 | 9 |
| 15 | 9 | 9 | 9 |
| 16 | 9 | 8 | 7 |
| 17 | 9 | 10 | 8 |
| 18 | 12 | 11 | 10 |
| 19 | 11 | 10 | 9 |
| 20 | 11 | 11 | 10 |
| 21 | 9 | 9 | 8 |
| 22 | 12 | 12 | 10 |
| Comparative product | | | |
| 1 | 5 | 5 | 3 |
| 2 | 6 | 5 | 6 |
| 3 | 5 | 5 | 4 |
| 4 | 6 | 5 | 5 |
| 5 | 5 | 4 | 4 |
| 6 | 6 | 6 | 5 |
| 7 | 6 | 6 | 4 |
| 8 | 7 | 7 | 5 |
| 9 | 6 | 6 | 5 |
| 10 | 6 | 5 | 6 |
| 11 | 5 | 5 | 4 |

Example 2

The number of days for the rose being preserved was examined in the same manner as in Example 1 except that the concentrations of sucrose and sucrose fatty acid ester were varied as shown in Table 3 (the balance is tap water) and then the freshness-keeping agents were used. The numbers in Table 3 indicate the number of days for the rose being preserved. It can be seen that the number of days therefor being preserved is significantly improved when the content of the sucrose fatty acid ester is in the range of 0.0001 to 0.1% by weight and when the ratio of the sucrose fatty acid ester to/sucrose by weight is in the range of 0.00001 to 2.0. The sucrose fatty acid ester is the same as in Example 1. The number of days for the rose being preserved was 5 in all cases where commercial products Chrysal and Repeat, both diluted 50-fold, were used.

TABLE 3

| Concentration of the sucrose | Concentration of the sucrose fatty acid ester (% by weight) | | | | |
|---|---|---|---|---|---|
| (% by weight) | 0 | 0.0001 | 0.001 | 0.01 | 0.1 |
| 0 | 3 | 3 | 4 | 4 | 3 |
| 0.1 | 3 | 8 | 9 | 10 | 7 |
| 0.5 | 4 | 8 | 11 | 12 | 7 |
| 1.0 | 5 | 9 | 13 | 14 | 8 |
| 2.0 | 5 | 10 | 15 | 15 | 8 |
| 5.0 | 5 | 10 | 12 | 11 | 7 |
| 10.0 | 3 | 10 | 11 | 10 | 7 |

Example 3

Commercial Chinese cabbage and spinach having most similar growth conditions and freshness conditions within the possibility were selected. Each individual leaf was harvested therefrom one after another and examined in the test. Each of the leaves was immersed for 5 minutes at the room temperature in the freshness-keeping agents prepared in Example 1 (Inventive product 1 to 22 and Comparative products 1 to 8, 10 and 11 in Table 1). Thereafter, each of the leaves was removed therefrom, left at the room temperature for 48 hours and then measured for the weight of the leaf as an indication of the maintenance of freshness. The relative weight of the leaf to the weight (100) of the leaf just before immersion is shown in results of Table 4. It was shown from Table 4 that, as compared with Comparative products, Inventive products were confirmed to have the effect of keeping the freshness of the vegetables in all test systems and the freshness-keeping effect of the sugar (B) and the sugar derivative- or sugar alcohol derivative-based surfactant (A) was thus recognized.

TABLE 4

| No. | The number of days for the vegetables being preserved | |
|---|---|---|
| | Chinese cabbage | Spinach |
| Inventive product | | |
| 1 | 90 | 92 |
| 2 | 92 | 96 |
| 3 | 90 | 94 |
| 4 | 94 | 95 |
| 5 | 95 | 95 |
| 6 | 92 | 94 |
| 7 | 91 | 93 |
| 8 | 90 | 90 |
| 9 | 93 | 94 |
| 10 | 92 | 94 |
| 11 | 95 | 96 |
| 12 | 87 | 90 |
| 13 | 91 | 92 |
| 14 | 90 | 94 |
| 15 | 89 | 90 |
| 16 | 90 | 93 |
| 17 | 92 | 95 |
| 18 | 93 | 91 |
| 19 | 86 | 91 |
| 20 | 90 | 90 |
| 21 | 90 | 91 |
| 22 | 93 | 93 |

TABLE 4-continued

| No. | The number of days for the vegetables being preserved | |
|---|---|---|
| | Chinese cabbage | Spinach |
| Comparative product | | |
| 1 | 80 | 85 |
| 2 | 83 | 87 |
| 3 | 82 | 88 |
| 4 | 83 | 87 |
| 5 | 83 | 86 |
| 6 | 83 | 85 |
| 7 | 83 | 86 |
| 8 | 83 | 87 |
| 10 | 83 | 85 |
| 11 | 80 | 85 |

Example 4

The same evaluation as in Example 1 was carried out except that Inventive products 23 to 35 and Comparative products 12 to 19 shown in Table 5 were used. The results are shown in Table 6. The sucrose fatty acid ester was the same as in Example 1. Unless otherwise specified, all reagents or the like used therein are those described in Example 1.

TABLE 6

| No. | chrysanthemum | carnation | rose |
|---|---|---|---|
| Inventive product | | | |
| 23 | 13 | 13 | 12 |
| 24 | 12 | 12 | 11 |
| 25 | 11 | 11 | 10 |
| 26 | 12 | 11 | 11 |
| 27 | 13 | 13 | 14 |
| 28 | 15 | 15 | 14 |
| 29 | 13 | 13 | 12 |
| 30 | 12 | 13 | 12 |
| 31 | 13 | 13 | 12 |
| 32 | 14 | 12 | 12 |
| 33 | 12 | 11 | 11 |
| 34 | 12 | 11 | 10 |
| 35 | 12 | 12 | 11 |
| Comparative product | | | |
| 12 | 5 | 5 | 3 |
| 13 | 6 | 6 | 5 |
| 14 | 6 | 6 | 6 |
| 15 | 5 | 5 | 4 |
| 16 | 5 | 5 | 5 |
| 17 | 5 | 4 | 4 |
| 18 | 7 | 7 | 5 |
| 19 | 6 | 6 | 5 |

TABLE 5

| No. | Sugar (B) | Sugar derivative- or sugar alcohol derivative-based surfactant (A) | Aggregating agent for colloidal particles (E) |
|---|---|---|---|
| Inventive product | | | |
| 23 | Fructose 1.0% + glucose 1.0% | Decyl polyglucoside 100 ppm | Aluminum sulfate with 13 to 14 $H_2O$ 0.05% |
| 24 | Fructose 1.0% + glucose 1.0% | Decyl polyglucoside 100 ppm | Calcium chloride with 2 $H_2O$ 0.1% |
| 25 | Fructose 1.0% + glucose 1.0% | Decyl polyglucoside 100 ppm | Kuriflock LC-541 0.005% |
| 26 | Fructose 1.0% + glucose 1.0% | Decyl polyglucoside 100 ppm | Chitosan 0.05% |
| 27 | Fructose 1.0% + glucose 1.0% | Sucrose fatty acid ester 100 ppm | Aluminum sulfate with 13.5 $H_2O$ 400 ppm |
| 28 | Fructose 1.0% + glucose 1.0% | Sucrose fatty acid ester 100 ppm | Aluminum sulfate with 13 to 14 $H_2O$ 0.05% |
| 29 | Fructose 1.0% + glucose 1.0% | Sucrose fatty acid ester 100 ppm | Calcium chloride with 2 $H_2O$ 0.1% |
| 30 | Fructose 1.0% + glucose 1.0% | Sucrose fatty acid ester 100 ppm | Kuriflock LC-541 0.005% |
| 31 | Fructose 1.0% + glucose 1.0% | Sucrose fatty acid ester 100 ppm | Chitosan 0.05% |
| 32 | Fructose 1.0% + glucose 1.0% | Sorbitan fatty acid ester 100 ppm | Aluminum sulfate with 13 to 14 $H_2O$ 0.05% |
| 33 | Fructose 1.0% + glucose 1.0% | Sorbitan fatty acid ester 100 ppm | Calcium chloride with 2 $H_2O$ 0.1% |
| 34 | Fructose 1.0% + glucose 1.0% | Sorbitan fatty acid ester 100 ppm | Kuriflock LC-541 0.005% |
| 35 | Fructose 1.0% + glucose 1.0% | Sorbitan fatty acid ester 100 ppm | Chitosan 0.05% |
| Comparative product | | | |
| 12 | Tap water | — | Tap water |
| 13 | Fructose 1.0% + glucose 1.0% | — | — |
| 14 | — | — | Aluminum sulfate with 13 to 14 $H_2O$ 0.05% |
| 15 | — | — | Calcium chloride with 2 $H_2O$ 0.1% |
| 16 | — | — | Kuriflock LC-541 0.005% |
| 17 | — | — | Chitosan 0.05% |
| 18 | — | — | Chrysal 2% (diluted to 50-hold) |
| 19 | — | — | Repeat 2% (diluted to 50-hold) |

Example 5

The same evaluation as in Example 1 was carried out except that Inventive products 36 to 48 and Comparative products 20 to 27 shown in Table 7 were used. The results are shown in Table 8. Unless otherwise specified, all reagents or the like used therein are those described in Example 1.

TABLE 7

|  | No. | Sugar (B) | Sugar derivative- or sugar alcohol derivative-based surfactant (A) | Aging inhibitor (D) |
|---|---|---|---|---|
| Inventive product | 36 | Fructose 1.0% + glucose 1.0% | Decyl polyglucoside 100 ppm | Silver thiosulfate 0.001% |
|  | 37 | Fructose 1.0% + glucose 1.0% | Decyl polyglucoside 100 ppm | Aminoisobutyric acid 0.3% |
|  | 38 | Fructose 1.0% + glucose 1.0% | Decyl polyglucoside 100 ppm | Sodium tetraborate with 10 $H_2O$ 0.01% |
|  | 39 | Fructose 1.0% + glucose 1.0% | Decyl polyglucoside 100 ppm | Ethionine 0.001% |
|  | 40 | Fructose 1.0% + glucose 1.0% | Sucrose fatty acid ester 100 ppm | Silver thiosulfate 0.001% |
|  | 41 | Fructose 1.0% + glucose 1.0% | Sucrose fatty acid ester 100 ppm | Silver thiosulfate 11 ppm (as the effective content) |
|  | 42 | Fructose 1.0% + glucose 1.0% | Sucrose fatty acid ester 100 ppm | Aminoisobutyric acid 0.3% |
|  | 43 | Fructose 1.0% + glucose 1.0% | Sucrose fatty acid ester 100 ppm | Sodium tetraborate with 10 $H_2O$ 0.01% |
|  | 44 | Fructose 1.0% + glucose 1.0% | Sucrose fatty acid ester 100 ppm | Ethionine 0.001% |
|  | 45 | Fructose 1.0% + glucose 1.0% | Sorbitan fatty acid ester 100 ppm | Silver thiosulfate 0.001% |
|  | 46 | Fructose 1.0% + glucose 1.0% | Sorbitan fatty acid ester 100 ppm | Aminoisobutyric acid 0.3% |
|  | 47 | Fructose 1.0% + glucose 1.0% | Sorbitan fatty acid ester 100 ppm | Sodium tetraborate with 10 $H_2O$ 0.01% |
|  | 48 | Fructose 1.0% + glucose 1.0% | Sorbitan fatty acid ester 100 ppm | Ethionine 0.001% |
| Comparative product | 20 | Tap water | — | Tap water |
|  | 21 | Fructose 1.0% + glucose 1.0% | — | — |
|  | 22 | — | — | Silver thiosulfate 0.001% |
|  | 23 | — | — | Aminoisobutyric acid 0.3% |
|  | 24 | — | — | Sodium tetraborate with 10 $H_2O$ 0.01% |
|  | 25 | — | — | Ethionine 0.001% |
|  | 26 | — | — | Chrysal 2% (diluted to 50-hold) |
|  | 27 | — | — | Repeat 2% (diluted to 50-hold) |

TABLE 8

|  | No. | chrysanthemum | carnation | rose |
|---|---|---|---|---|
| Inventive product | 36 | 13 | 13 | 13 |
|  | 37 | 12 | 12 | 12 |
|  | 38 | 13 | 12 | 13 |
|  | 39 | 13 | 13 | 13 |
|  | 40 | 15 | 15 | 14 |
|  | 41 | 14 | 13 | 14 |
|  | 42 | 13 | 13 | 13 |
|  | 43 | 12 | 13 | 12 |
|  | 44 | 12 | 14 | 13 |
|  | 45 | 14 | 14 | 15 |
|  | 46 | 12 | 13 | 13 |
|  | 47 | 13 | 14 | 13 |
|  | 48 | 13 | 13 | 13 |
| Comparative product | 20 | 5 | 5 | 3 |
|  | 21 | 6 | 6 | 5 |
|  | 22 | 7 | 7 | 5 |
|  | 23 | 6 | 5 | 4 |
|  | 24 | 6 | 6 | 4 |
|  | 25 | 6 | 6 | 5 |
|  | 26 | 7 | 7 | 4 |
|  | 27 | 6 | 6 | 4 |

Example 6

The same evaluation as in Example 1 was conducted except that Inventive products 49 to 58 and Comparative products 28 to 34 shown in Table 9 were used. The results are shown in Table 10. Unless otherwise specified, all reagents or the like used therein are those described in Example 1.

TABLE 9

|  | No. | Sugar (B) | Sugar derivative- or sugar alcohol derivative-based surfactant (A) | Plant hormone (C) |
|---|---|---|---|---|
| Inventive product | 49 | Fructose 1.0% + glucose 1.0% | Decyl polyglucoside 100 ppm | Gibberellin (GA3) 1 ppm |
|  | 50 | Fructose 1.0% + glucose 1.0% | Decyl polyglucoside 100 ppm | Kinetin 1 ppm |
|  | 51 | Fructose 1.0% + glucose 1.0% | Decyl polyglucoside 100 ppm | 2, 4-D 10 ppm |
|  | 52 | Fructose 1.0% + glucose 1.0% | Sucrose fatty acid ester 100 ppm | Gibberellin (GA3) 1 ppm |
|  | 53 | Fructose 1.0% + glucose 1.0% | Sucrose fatty acid ester 100 ppm | Gibberellin (GA3) 5 ppm |
|  | 54 | Fructose 1.0% + glucose 1.0% | Sucrose fatty acid ester 100 ppm | Kinetin 1 ppm |
|  | 55 | Fructose 1.0% + glucose 1.0% | Sucrose fatty acid ester 100 ppm | 2, 4-D 10 ppm |
|  | 56 | Fructose 1.0% + glucose 1.0% | Sorbitan fatty acid ester 100 ppm | Gibberellin (GA3) 1 ppm |
|  | 57 | Fructose 1.0% + glucose 1.0% | Sorbitan fatty acid ester 100 ppm | Kinetin 1 ppm |

TABLE 9-continued

| | No. | Sugar (B) | Sugar derivative- or sugar alcohol derivative-based surfactant (A) | Plant hormone (C) |
|---|---|---|---|---|
| | 58 | Fructose 1.0% + glucose 1.0% | Sorbitan fatty acid ester 100 ppm | 2, 4-D 10 ppm |
| Comparative product | 28 | Tap water | — | Tap water |
| | 29 | Fructose 1.0% + glucose 1.0% | — | — |
| | 30 | — | — | Gibberellin (GA3) 1 ppm |
| | 31 | — | — | Kinetin 1 ppm |
| | 32 | — | — | 2, 4-D 10 ppm |
| | 33 | — | — | Chrysal 2% (diluted to 50-hold) |
| | 34 | — | — | Repeat 2% (diluted to 50-hold) |

TABLE 10

| | No. | chrysanthemum | carnation | rose |
|---|---|---|---|---|
| Inventive product | 49 | 15 | 15 | 14 |
| | 50 | 14 | 14 | 13 |
| | 51 | 13 | 13 | 12 |
| | 52 | 17 | 17 | 16 |
| | 53 | 14 | 15 | 13 |
| | 54 | 15 | 15 | 14 |
| | 55 | 14 | 15 | 14 |
| | 56 | 16 | 14 | 14 |
| | 57 | 14 | 13 | 13 |
| | 58 | 14 | 13 | 12 |
| Comparative product | 28 | 5 | 5 | 3 |
| | 29 | 6 | 6 | 5 |
| | 30 | 4 | 4 | 3 |
| | 31 | 5 | 4 | 4 |
| | 32 | 4 | 4 | 3 |
| | 33 | 7 | 7 | 5 |
| | 34 | 6 | 6 | 5 |

TABLE 12

| | No. | chrysanthemum | carnation | rose |
|---|---|---|---|---|
| Inventive product | 59 | 13 | 13 | 12 |
| | 60 | 12 | 12 | 11 |
| | 61 | 11 | 11 | 10 |
| | 62 | 15 | 15 | 14 |
| | 63 | 13 | 13 | 12 |
| | 64 | 12 | 13 | 12 |
| | 65 | 13 | 13 | 13 |
| | 66 | 14 | 12 | 12 |
| | 67 | 12 | 11 | 11 |
| | 68 | 12 | 11 | 10 |
| Comparative product | 35 | 5 | 5 | 3 |
| | 36 | 6 | 6 | 5 |
| | 37 | 4 | 4 | 3 |
| | 38 | 5 | 4 | 4 |
| | 39 | 4 | 4 | 3 |
| | 40 | 7 | 7 | 5 |
| | 41 | 6 | 6 | 5 |

Example 7

The same evaluation as in Example 1 was carried out except that Inventive products 59 to 68 and Comparative products 35 to 41 shown in Table 11 were used. The results are shown in Table 12. Unless otherwise specified, all reagents or the like used therein are those described in Example 1.

Example 8

Those freshness-keeping agents having the compositions shown in Table 13 were prepared (Inventive products 69 to 86 and Comparative products 42 to 50). In Table 13, the balance is tap water.

TABLE 11

| | No. | Sugar (B) | Sugar derivative- or sugar alcohol derivative-based surfactant (A) | Germicide, fungicide or preservative (F) |
|---|---|---|---|---|
| Inventive product | 59 | Fructose 1.0% + glucose 1.0% | Decyl polyglucoside 100 ppm | 8-hydroxyquinoline 500 ppm |
| | 60 | Fructose 1.0% + glucose 1.0% | Decyl polyglucoside 100 ppm | Proxel 200 ppm |
| | 61 | Fructose 1.0% + glucose 1.0% | Decyl polyglucoside 100 ppm | Didecyl dimethyl ammonium chloride 5 ppm |
| | 62 | Fructose 1.0% + glucose 1.0% | Sucrose fatty acid ester 100 ppm | 8-hydroxyquinoline 500 ppm |
| | 63 | Fructose 1.0% + glucose 1.0% | Sucrose fatty acid ester 100 ppm | Proxel 200 ppm |
| | 64 | Fructose 1.0% + glucose 1.0% | Sucrose fatty acid ester 100 ppm | Didecyl dimethyl ammonium chloride 5 ppm |
| | 65 | Fructose 1.0% + glucose 1.0% | Sucrose fatty acid ester 100 ppm | Didecyl dimethyl ammonium chloride 10 ppm |
| | 66 | Fructose 1.0% + glucose 1.0% | Sorbitan fatty acid ester 100 ppm | 8-hydroxyquinoline 500 ppm |
| | 67 | Fructose 1.0% + glucose 1.0% | Sorbitan fatty acid ester 100 ppm | Proxel 200 ppm |
| | 68 | Fructose 1.0% + glucose 1.0% | Sorbitan fatty acid ester 100 ppm | Didecyl dimethyl ammonium chloride 5 ppm |
| Comparative product | 35 | Tap water | — | Tap water |
| | 36 | Fructose 1.0% + glucose 1.0% | — | — |
| | 37 | — | — | 8-hydroxyquinoline 500 ppm |
| | 38 | — | — | Proxel 200 ppm |
| | 39 | — | — | didecyl dimethyl ammonium chloride 5 ppm |
| | 40 | — | — | Chrysal 2% (diluted to 50-hold) |
| | 41 | — | — | Repeat 2% (diluted to 50-hold) |

TABLE 13

| | No. | Aggregating agent for colloidal particles (E) | Surfactant (A) |
|---|---|---|---|
| Inventive product | 69 | Aluminum sulfate with 13 to 14 $H_2O$ 0.05% | Decyl polyglucoside 100 ppm |
| | 70 | Calcium chloride with 2 $H_2O$ 0.1%. | Decyl polyglucoside 100 ppm |
| | 71 | Kuriflock LC-541 0.005% | Decyl polyglucoside 100 ppm |
| | 72 | Chitosan 0.05% | Decyl polyglucoside 100 ppm |
| | 73 | Aluminum sulfate with 13 to 14 $H_2O$ 0.05% + Kuriflock LC-541 0.005% | Decyl polyglucoside 100 ppm |
| | 74 | Aluminum sulfate with 13 to 14 $H_2O$ 0.05% + Chitosan 0.05% | Decyl polyglucoside 100 ppm |
| | 75 | Aluminum sulfate with 13 to 14 $H_2O$ 0.05% | Sucrose fatty acid ester 100 ppm |
| | 76 | Calcium chloride with 2 $H_2O$ 0.1% | Sucrose fatty acid ester 100 ppm |
| | 77 | Kuriflock LC-541 0.005% | Sucrose fatty acid ester 100 ppm |
| | 78 | Chitosan 0.05% | Sucrose fatty acid ester 100 ppm |
| | 79 | Aluminum sulfate with 13 to 14 $H_2O$ 0.05% + Kuriflock LC-541 0.005% | Sucrose fatty acid ester 100 ppm |
| | 80 | Aluminum sulfate with 13 to 14 $H_2O$ 0.05% + Chitosan 0.05% | Sucrose fatty acid ester 100 ppm |
| | 81 | Aluminum sulfate with 13 to 14 $H_2O$ 0.05% | Sorbitan fatty acid ester 100 ppm |
| | 82 | Calcium chloride with 2 $H_2O$ 0.1% | Sorbitan fatty acid ester 100 ppm |
| | 83 | Kuriflock LC-541 0.005% | Sorbitan fatty acid ester 100 ppm |
| | 84 | Chitosan 0.05% | Sorbitan fatty acid ester 100 ppm |
| | 85 | Aluminum sulfate with 13 to 14 $H_2O$ 0.05% + Kuriflock LC-541 0.005% | Sorbitan fatty acid ester 100 ppm |
| | 86 | Aluminum sulfate with 13 to 14 $H_2O$ 0.05% + Chitosan 0.05% | Sorbitan fatty acid ester 100 ppm |
| Comparative product | 42 | Tap water | — |
| | 43 | Aluminum sulfate with 13 to 14 $H_2O$ 0.05% | — |
| | 44 | Calcium chloride with 2 $H_2O$ 0.1% | — |
| | 45 | Kuriflock LC-541 0.005% | — |
| | 46 | Chitosan 0.05% | — |
| | 47 | Aluminum sulfate with 13 to 14 $H_2O$ 0.05% + Kuriflock LC-541 0.005% | — |
| | 48 | Aluminum sulfate with 13 to 14 $H_2O$ 0.05% + Chitosan 0.05% | — |
| | 49 | Chrysal 2% (diluted to 50-hold) | — |
| | 50 | Repeat 2% (diluted to 50-hold) | — |

(Notes)

Kuriflock LC-541: Cationic polymer aggregate with a molecular weight of 1,000,000, Kurita Water Industries Ltd.

Chrysal: described above.

Repeat: described above.

Decyl polyglucoside: described above.

Sucrose fatty acid ester: described above.

Sorbitan fatty acid ester: described above.

The same evaluation as in Example 1 was carried out except that Inventive products 69 to 86 and Comparative products 42 to 50 were used as the freshness-keeping agents.

The results are shown in Table 14. As compared with Comparative products, Inventive products were confirmed to have the effect for the flowers being preserved in all test systems, and the freshness-keeping effect of the sugar derivative- or sugar alcohol derivative-based surfactant (A) was thus recognized.

TABLE 14

| | | The number of days for the flowers being preserved | | |
|---|---|---|---|---|
| | No. | chrysanthemum | carnation | rose |
| Inventive product | 69 | 10 | 10 | 9 |
| | 70 | 9 | 9 | 8 |
| | 71 | 8 | 8 | 7 |
| | 72 | 9 | 8 | 8 |
| | 73 | 12 | 11 | 10 |
| | 74 | 13 | 11 | 8 |
| | 75 | 12 | 12 | 11 |
| | 76 | 10 | 10 | 9 |
| | 77 | 9 | 10 | 9 |
| | 78 | 10 | 10 | 9 |
| | 79 | 13 | 13 | 12 |
| | 80 | 14 | 13 | 12 |
| | 81 | 11 | 9 | 9 |
| | 82 | 9 | 8 | 8 |
| | 83 | 9 | 8 | 7 |
| | 84 | 9 | 9 | 8 |
| | 85 | 12 | 10 | 10 |

TABLE 14-continued

| | | The number of days for the flowers being preserved | | |
|---|---|---|---|---|
| | No. | chrysanthemum | carnation | rose |
| | 86 | 12 | 10 | 11 |
| Comparative product | 42 | 5 | 5 | 3 |
| | 43 | 6 | 6 | 6 |
| | 44 | 5 | 5 | 4 |
| | 45 | 5 | 5 | 5 |
| | 46 | 5 | 4 | 4 |
| | 47 | 6 | 6 | 6 |
| | 48 | 6 | 6 | 6 |
| | 49 | 7 | 7 | 5 |
| | 50 | 6 | 6 | 5 |

Example 9

The same test as in Example 1 was carried out except that Inventive products and Comparative products shown in Table 15 were used. The results are shown in Table 16. As compared with Comparative products, Inventive products were confirmed to increase the days for the flowers being preserved in all test systems, and the freshness-keeping effect of the aggregating agent for colloidal particles (E) and the sugar derivative- or sugar alcohol derivative-based surfactant (A) was thus recognized. The decyl polyglucoside and sucrose fatty acid ester are the same as in Example 1.

TABLE 15

|  | No. | Aggregating agent for colloidal particles (E) | Surfactant (A) |
|---|---|---|---|
| Inventive product | 87 | Aluminum sulfate with 13 to 14 H$_2$O 0.05% | Decyl polyglucoside 1 ppm |
|  | 88 | Aluminum sulfate with 13 to 14 H$_2$O 0.05% | Decyl polyglucoside 10 ppm |
|  | 89 | Aluminum sulfate with 13 to 14 H$_2$O 0.05% | Decyl polyglucoside 100 ppm |
|  | 90 | Aluminum sulfate with 13 to 14 H$_2$O 0.05% | Decyl polyglucoside 1000 ppm |
|  | 91 | Aluminum sulfate with 13 to 14 H$_2$O 0.05% | Sucrose fatty acid ester 1 ppm |
|  | 92 | Aluminum sulfate with 13 to 14 H$_2$O 0.05% | Sucrose fatty acid ester 10 ppm |
|  | 93 | Aluminum sulfate with 13 to 14 H$_2$O 0.05% | Sucrose fatty acid ester 100 ppm |
|  | 94 | Aluminum sulfate with 13 to 14 H$_2$O 0.05% | Sucrose fatty acid ester 1000 ppm |
| Comparative product | 51 | Tap water | — |
|  | 52 | Aluminum sulfate with 13 to 14 H$_2$O 0.05% | — |
|  | 53 | Chrysal 2% (diluted to 50-hold) | — |
|  | 54 | Repeat 2% (diluted to 50-hold) | — |

TABLE 16

|  |  | The number of days for the flowers being preserved | | |
|---|---|---|---|---|
|  | No. | chrysanthemum | carnation | rose |
| Inventive product | 87 | 8 | 8 | 7 |
|  | 88 | 11 | 10 | 10 |
|  | 89 | 12 | 12 | 10 |
|  | 90 | 7 | 9 | 7 |
|  | 91 | 9 | 9 | 8 |
|  | 92 | 12 | 11 | 11 |
|  | 93 | 13 | 12 | 12 |
|  | 94 | 9 | 9 | 8 |
| Comparative product | 51 | 5 | 5 | 3 |
|  | 52 | 7 | 7 | 5 |
|  | 53 | 7 | 7 | 4 |
|  | 54 | 6 | 6 | 4 |

Example 10

Commercial Chinese cabbage and spinach having most similar freshness conditions and growth conditions with the possibility were selected. Each individual leaf was harvested therefrom one after another and examined in the test. Each of the leaves was immersed for 5 minutes at the room temperature in the freshness-keeping agents (the products prepared in Example 1) shown in Table 5. Thereafter, each of the leaves was removed therefrom, left at the room temperature for 48 hours and then measured for the weight of the leaf as an indication of the maintenance of freshness. The relative weight of the leaf to the weight (=100) of the leaf just before immersion is shown in results of Table 17. As compared with Comparative product, Inventive products were confirmed to have the effect of keeping the freshness of the vegetables in all test systems and the freshness-keeping effect of the aggregating agent for colloidal particles (E) and the sugar derivative-based surfactant, the sugar derivative- or sugar alcohol derivative-based surfactant (A) was thus recognized.

TABLE 17

|  | No. | Chinese cabbage | Spinach |
|---|---|---|---|
| Inventive product | 69 | 92 | 92 |
|  | 70 | 89 | 90 |
|  | 71 | 90 | 91 |
|  | 72 | 90 | 91 |
|  | 73 | 95 | 93 |
|  | 74 | 95 | 93 |
|  | 75 | 94 | 93 |
|  | 76 | 92 | 91 |
|  | 77 | 92 | 92 |
|  | 78 | 93 | 92 |
|  | 79 | 96 | 95 |
|  | 80 | 96 | 95 |
|  | 81 | 90 | 94 |
|  | 82 | 89 | 91 |
|  | 83 | 89 | 92 |
|  | 84 | 88 | 91 |
|  | 85 | 92 | 94 |
|  | 86 | 91 | 95 |
| Comparative product | 42 | 80 | 85 |
|  | 43 | 83 | 87 |
|  | 44 | 81 | 86 |
|  | 45 | 82 | 86 |
|  | 46 | 82 | 86 |
|  | 47 | 85 | 88 |
|  | 48 | 85 | 88 |
|  | 49 | 83 | 87 |

Example 11

Those freshness-keeping agents having the compositions shown in Table 18 were prepared (Inventive products 95 to 112 and Comparative products 55 to 63). In Table 18, the balance is tap water.

TABLE 18

| | No. | Aging inhibitor (D) | Surfactant (A) |
|---|---|---|---|
| Inventive product | 95 | Silver thiosulfate 0.001%(in terms of silver) | Decyl polyglucoside 100 ppm |
| | 96 | Aminoisobutyric acid 0.3% | Decyl polyglucoside 100 ppm |
| | 97 | Sodium tetraborate with 10 $H_2O$ 0.01% | Decyl polyglucoside 100 ppm |
| | 98 | Ethionine 0.001% | Decyl polyglucoside 100 ppm |
| | 99 | Aminoethoxy vinyl glycine 0.05% | Decyl polyglucoside 100 ppm |
| | 100 | Silver thiosulfate 0.001%(in terms of silver) + Aminoisobutyric acid 0.3% | Decyl polyglucoside 100 ppm |
| | 101 | Silver thiosulfate 0.001%(in terms of silver) | Sucrose fatty acid ester 100 ppm |
| | 102 | Aminoisobutyric acid 0.3% | Sucrose fatty acid ester 100 ppm |
| | 103 | Sodium tetraborate with 10 $H_2O$ 0.01% | Sucrose fatty acid ester 100 ppm |
| | 104 | Ethionine 0.001% | Sucrose fatty acid ester 100 ppm |
| | 105 | Aminoethoxy vinyl glycine 0.05% | Sucrose fatty acid ester 100 ppm |
| | 106 | Silver thiosulfate 0.001%(in terms of silver) + Aminoisobutyric acid 0.3% | Sucrose fatty acid ester 100 ppm |
| | 107 | Silver thiosulfate 0.001%(in terms of silver) | Sorbitan fatty acid ester 100 ppm |
| | 108 | Aminoisobutyric acid 0.3% | Sorbitan fatty acid ester 100 ppm |
| | 109 | Sodium tetraborate with 10 $H_2O$ 0.01% | Sorbitan fatty acid ester 100 ppm |
| | 110 | Ethionine 0.001% | Sorbitan fatty acid ester 100 ppm |
| | 111 | Aminoethoxy vinyl glycine 0.05% | Sorbitan fatty acid ester 100 ppm |
| | 112 | Silver thiosulfate 0.001%(in terms of silver) + Aminoisobutyric acid 0.3% | Sorbitan fatty acid ester 100 ppm |
| Comparative product | 55 | Tap water | — |
| | 56 | Silver thiosulfate 0.001%(in terms of silver) | — |
| | 57 | Aminoisobutyric acid 0.3% | — |
| | 58 | Sodium tetraborate with 10 $H_2O$ 0.01% | — |
| | 59 | Ethionine 0.001% | — |
| | 60 | Aminoethoxy vinyl glycine 0.05% | — |
| | 61 | Silver thiosulfate 0.001%(in terms of silver) + Aminoisobutyric acid 0.3% | — |
| | 62 | Chrysal 2% (diluted to 50-hold) | — |
| | 63 | Repeat 2% (diluted to 50-hold) | — |

(Notes)

Silver thiosulfate: Koto Fresh K20C, Koto Co., Ltd.

Aminoethoxy vinyl glycine: Flourish, Tomen Corporation Ltd.

Chrysal: described above.

Repeat: described above.

Decyl polyglucoside: described above.

Sucrose fatty acid ester: described above.

Sorbitan fatty acid ester: described above.

The same evaluation as in Example 1 was carried out except that Inventive products 95 to 112 and Comparative products 55 to 63 were used as the freshness-keeping agents.

The results are shown in Table 19. As compared with Comparative products, Inventive products were confirmed to have the effect for the flowers being preserved in all test systems, and the freshness-keeping effect of the sugar derivative- or sugar alcohol derivative-based surfactant (A) was thus recognized.

TABLE 19

| | | The number of days for the flowers being preserved | | |
|---|---|---|---|---|
| | No. | chrysanthemum | carnation | rose |
| Inventive product | 95 | 9 | 9 | 9 |
| | 96 | 8 | 8 | 8 |
| | 97 | 9 | 8 | 9 |
| | 98 | 9 | 9 | 9 |
| | 99 | 8 | 8 | 9 |
| | 100 | 10 | 10 | 9 |
| | 101 | 11 | 11 | 10 |
| | 102 | 9 | 9 | 9 |
| | 103 | 8 | 9 | 8 |
| | 104 | 8 | 10 | 9 |
| | 105 | 9 | 10 | 8 |
| | 106 | 11 | 10 | 10 |
| | 107 | 10 | 10 | 11 |
| | 108 | 8 | 9 | 9 |
| | 109 | 9 | 10 | 9 |
| | 110 | 9 | 9 | 9 |
| | 111 | 9 | 10 | 9 |
| | 112 | 10 | 10 | 10 |
| Comparative product | 55 | 5 | 5 | 3 |
| | 56 | 7 | 7 | 5 |
| | 57 | 6 | 5 | 4 |
| | 58 | 6 | 6 | 4 |
| | 59 | 6 | 6 | 5 |
| | 60 | 6 | 6 | 5 |
| | 61 | 7 | 7 | 6 |
| | 62 | 7 | 7 | 4 |
| | 63 | 6 | 6 | 4 |

Example 12

The same test as in Example 1 was carried out except that the Inventive products and Comparative products shown in Table 20 were used. The results are shown in Table 21. As compared with Comparative products, Inventive products were confirmed to increase the days for the flowers being preserved in all test systems, and the freshness-keeping effect of the aging inhibitor (D) and the sugar derivative- or sugar alcohol derivative-based surfactant (A) was thus recognized. The silver thionitrate, decyl polyglucoside and sucrose fatty acid ester are the same as in Examples 1 and 11.

TABLE 20

| | No. | Aging inhibitor (D) | Surfactant (A) |
|---|---|---|---|
| Inventive product | 113 | silver thiosulfate 0.001%(in terms of silver) | Decyl polyglucoside 1 ppm |
| | 114 | silver thiosulfate 0.001%(in terms of silver) | Decyl polyglucoside 10 ppm |
| | 115 | silver thiosulfate 0.001%(in terms of silver) | Decyl polyglucoside 100 ppm |
| | 116 | silver thiosulfate 0.001%(in terms of silver) | Decyl polyglucoside 1000 ppm |
| | 117 | silver thiosulfate 0.001%(in terms of silver) | Sucrose fatty acid ester 1 ppm |
| | 118 | silver thiosulfate 0.001%(in terms of silver) | Sucrose fatty acid ester 10 ppm |
| | 119 | silver thiosulfate 0.001%(in terms of silver) | Sucrose fatty acid ester 100 ppm |
| | 120 | silver thiosulfate 0.001%(in terms of silver) | Sucrose fatty acid ester 1000 ppm |
| Comparative product | 64 | Tap water | — |
| | 65 | silver thiosulfate 0.001%(in terms of silver) | — |
| | 66 | Chrysal 2% (diluted to 50-fold) | — |
| | 67 | Repeat 2% (diluted to 50-fold) | — |

TABLE 21

| | | The number of days for the flowers being preserved | | |
|---|---|---|---|---|
| | No. | chrysanthemum | carnation | rose |
| Inventive product | 113 | 9 | 9 | 8 |
| | 114 | 11 | 10 | 9 |
| | 115 | 9 | 9 | 9 |
| | 116 | 8 | 9 | 8 |
| | 117 | 10 | 9 | 9 |
| | 118 | 12 | 14 | 13 |
| | 119 | 11 | 11 | 10 |
| | 120 | 9 | 10 | 9 |
| Comparative product | 64 | 5 | 5 | 3 |
| | 65 | 7 | 7 | 5 |
| | 66 | 7 | 7 | 4 |
| | 67 | 6 | 6 | 4 |

Preferable products in the present invention are Inventive products 5, 7, 11, 18 and 22, those products showing 10 or more days for the plant being preserved in Table 3, and Inventive products 27, 28, 32, 40, 41, 45, 52, 53, 56, 62, 64 to 66, 68, 75, 79 to 81, 85, 86, 91 to 94, 101, 106, 107, 112 and 117 to 120. More preferable products are Inventive products 11 and 18, those products showing 15 or more days for the plant being preserved in Table 3, and Inventive products 27, 28, 40, 52, 53, 64, 65, 75, 79 to 81, 85, 86, 91 to 94, 101, 106, 107, 112 and 117 to 120.

The invention claimed is:

1. A harvested plant freshness-keeping composition comprising at least one surfactant (A), wherein said surfactant has a sugar structure or a sugar alcohol structure, and at least one selected from the group consisting of a sugar (B), a plant hormone (C), an aging inhibitor (D), an aggregating agent for colloidal particles (E) and a germicide, fungicide or preservative (F);
wherein either a hydrophobic group is bound via a glycoside linkage to the sugar or sugar alcohol in the component (A) and said component (A) is at a concentration of 0.0001 to 0.1 percent by weight of said composition,
a hydrophobic group is bound via an ester linkage to the sugar or sugar alcohol in the component (A), or
a hydrophobic group is bound via an amide linkage to the sugar or sugar alcohol in the component (A);
the ratio of (A)/(B) by weight is 0.00001 to 2.0; the ratio of (A)/(C) by weight is 0.0002 to 10000; the ratio of (D)/(A) by weight is 0.0002 to 1000; the ratio of (A)/(E) by weight is 0.0002 to 1000; or the ratio of (A)/(F) by weight is 0.00001 to 200;
component (C) is at least one selected from the group consisting of a natural auxin, synthetic auxin, natural cytokinin, synthetic cytokinin and gibberellin; and
said composition comprises 0.0001 to 0.5% by weight of component (F).

2. The harvested plant freshness-keeping composition as claimed in claim 1, wherein the sugar (B) is at least one selected from a monosaccharide, oligosaccharide and polysaccharide.

3. The harvested plant freshness-keeping composition as claimed in claim 1, wherein the aging inhibitor (D) is selected from the group consisting of: aminoethoxyvinyl glycine, aminooxyacetate hemihydrochloride, isopropyridine-aminooxyacetate-2-methoxy-2-oxoethyl ester, silver thiosulfate, silver thiosulfate complex salt, aminoisobutyric acid, 1,1-dimethyl-4-(phenyl sulfonyl) semicarbazide, cispropenyl phosphonic acid, sodium tetraborate, allocoronamic acid, aminotriazole, phenanthroline, diazocyclopentadiene, isothiocyanic acid allyl ester, 2,5-norbornadiene, 1-methyl cyclopropene and ethionine.

4. The harvested plant freshness-keeping composition as claimed in claim 1, wherein the aggregating agent for colloidal particles (E) is selected from the group consisting of: an aluminum compound, a calcium chloride, a combination of calcium chloride and phosphoric acid, and a polymer aggregate.

5. The harvested plant freshness-keeping composition as claimed in claim 1, wherein the germicide, fungicide or preservative (F) is selected from the group consisting of: sodium hypochlorite, copper sulfate, 8-hydroxyquinoline, ethanol, isopropanol, methyl p-hydroxybenzolate, ethyl p-hydroxybenzolate, propyl p-hydroxybenzolate, butyl p-hydroxybenzolate, 1,2-benzisothiazolin-3-one, a compound represented by the formula:

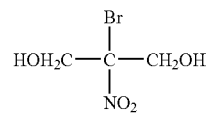

or a cationic surfactant.

6. The harvested plant freshness-keeping composition as claimed in claim 1, wherein the hydrophobic group is bound via the ester linkage to the sugar or sugar alcohol in the component (A), and the component (A) is selected from the group consisting of: a sorbitan fatty acid ester, a polyoxyalkylene sorbitan fatty acid ester, a sucrose fatty acid ester, a sorbitol fatty acid ester, a polyoxyalkylene sorbitol fatty acid ester, a polyglycerol, a polyglycerol fatty acid ester, a glycerol fatty acid ester and a polyoxyalkylene glycerol fatty acid ester.

7. The harvested plant freshness-keeping composition of claim 1, wherein the ratio (A)/(B) by weight is 0.0001 to 1.0; the ratio of (A)/(C) by weight is 0.001 to 1000; the ratio of (D)/(A) by weight is 0.0002 to 1000; the ratio of (A)/(E) by weight is 0.0002 to 20; or the ratio of (A)/(F) by weight is 0.0001 to 100.

8. The harvested plant freshness-keeping composition of claim 1, wherein said hydrophobic group is bound via the ester linkage to the sugar or sugar alcohol in the component (A), and said component (A) is at a concentration of 0.0001 to 0.1 percent by weight of said composition.

9. The harvested plant freshness-keeping composition of claim 1, wherein said component (A) is an alkyl polyglycoside having 10 to 18 carbon atoms in the hydrophobic group thereof.

10. A harvested plant freshness-keeping composition comprising at least one surfactant (A), wherein said surfactant has a sugar structure or a sugar alcohol structure, and at least one selected from the group consisting of a sugar (B), a plant hormone (C), an aging inhibitor (D), an aggregating agent for colloidal particles (E) and a germicide, fungicide or preservative (F);
    wherein a hydrophobic group is bound via a glycoside linkage to the sugar or sugar alcohol in the component (A) and said component (A) is at a concentration of 0.0001 to 0.1 percent by weight of said composition; and
    the component (A) is selected from the group consisting of an alkyl glycoside, an alkyl polyglycoside, a polyoxyalkylene alkyl (poly)glycoside, an alkyl (poly)glycoside sulfate comprising an alkyl (poly)glucoside sulfated therein, a phosphated alkyl (poly)glycoside, a glyceryl etherified alkyl (poly)glycoside, a sulfosuccinated alkyl (poly)glycoside, a glyceryl-esterified alkyl (poly)glycoside, a carboxy-alkylated alkyl (poly)glycoside, a cationic alkyl (poly)glycoside, and a betaine alkyl (poly)glycoside.

11. The harvested plant freshness-keeping composition of claim 10, wherein said component (A) is an alkyl polyglycoside having 10 to 18 carbon atoms in the hydrophobic group thereof.

12. A harvested plant freshness-keeping composition comprising at least one surfactant (A), wherein said surfactant has a sugar structure or a sugar alcohol structure, and at least one selected from the group consisting of a sugar (B), a plant hormone (C), an aging inhibitor (D), an aggregating agent for colloidal particles (E) and a germicide, fungicide or preservative (F);
    wherein either a hydrophobic group is bound via a glycoside linkage to the sugar or sugar alcohol in the component (A) and said component (A) is at a concentration of 0.0001 to 0.1 percent by weight of said composition, or
    a hydrophobic group is bound via an amide linkage to the sugar or sugar alcohol in the component (A);
    wherein the component (A) is a sugar-based fatty acid amide represented by the formula (1):

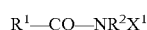

wherein $R^1$ is a $C_{5-17}$ linear or branched alkyl, alkenyl or alkylphenyl group, $R^2$ is hydrogen, a $C_{1-18}$ linear or branched alkyl or alkenyl group, $-(CH_2CH(R^3)O)_c-$H, wherein $R^3$ is hydrogen or a methyl group and c is a number selected from 0 to 10, $CH_2CH_2OH$, $-CH_2CH(OH)CH_3$ or $-CH_2CH_2CH_2OH$, and $X^1$ is a polyhydroxy alkyl group comprising a $C_{4-30}$ sugar residue.

13. The harvested plant freshness-keeping composition of claim 12, wherein said component (A) is an alkyl polyglycoside having 10 to 18 carbon atoms in the hydrophobic group thereof.

14. A harvested plant freshness-keeping composition comprising at least one surfactant (A) and at least one selected from the group consisting of a sugar (B), a plant hormone (C), an aging inhibitor (D), an aggregating agent for colloidal particles (E) and a germicide, fungicide or preservative (F);
    wherein component (A) is sorbitan fatty acid ester, component (B) is selected from the group consisting of glucose, sucrose and fructose, and component (C) is gibberellin;
    wherein a hydrophobic group is bound via an ester linkage to said component (A), and said component (A) is at a concentration of 0.0001 to 0.1 percent by weight of said composition.

15. A method of preserving a plant with keeping the freshness thereof, said method comprising:
    applying an effective amount of a plant freshness-keeping composition to said plant, wherein said plant freshness-keeping composition comprises at least one surfactant (A), wherein said surfactant has a sugar structure or a sugar alcohol structure, and at least one selected from the group consisting of a sugar (B), a plant hormone (C), an aging inhibitor (D), an aggregating agent for colloidal particles (E) and a germicide, fungicide or preservative (F),
    wherein either a hydrophobic group is bound via a glycoside linkage to the sugar or sugar alcohol in the component (A) and said component (A) is at a concentration of 0.0001 to 0.1 percent by weight of said composition,
    a hydrophobic group is bound via an ester linkage to the sugar or sugar alcohol in the component (A), or
    a hydrophobic group is bound via an amide linkage to the sugar or sugar alcohol in the component (A);
    wherein the plant is a harvested plant.

16. The method of preserving a harvested plant with a composition by keeping the freshness thereof of claim 15, wherein the component (A) of the plant freshness-keeping composition is an alkyl polyglycoside having 8 to 18 carbon atoms in the hydrophobic group thereof.

17. A method of preserving a plant with a composition by keeping the freshness thereof, comprising the steps of:
    a) obtaining a sample comprising said composition, where said composition is in the form of aqueous solution or powder; and
    b) applying said sample onto the plant;
    wherein said composition comprises at least one surfactant (A), wherein said surfactant has a sugar structure or a sugar alcohol structure, and at least one selected from the group consisting of a sugar (B), a plant hormone (C), an aging inhibitor (D), an aggregating agent for colloidal particles (E) and a germicide, fungicide or preservative (F);
    said plant is a harvested plant; and
    either a hydrophobic group is bound via a glycoside linkage to the sugar or sugar alcohol in the component (A) and said component (A) is at a concentration of 0.0001 to 0.1 percent by weight of said composition,
    a hydrophobic group is bound via an ester linkage to the sugar or sugar alcohol in the component (A), or a hydrophobic group is bound via an amide linkage to the sugar or sugar alcohol in the component (A).

18. The method of preserving a harvested plant with a composition by keeping the freshness thereof of claim 17, wherein the component (A) of the plant freshness-keeping composition is an alkyl polyglycoside having 8 to 18 carbon atoms in the hydrophobic group thereof.

19. The method of claim 17, wherein said component (A) is an alkyl polyglycoside having 10 to 18 carbon atoms in the hydrophobic group thereof.

20. A harvested plant freshness-keeping composition comprising at least one surfactant (A) and at least one selected from the group consisting of a sugar (B), a plant hormone (C), an aging inhibitor (D), an aggregating agent for colloidal particles (E) and a germicide, fungicide or preservative (F); wherein a hydrophobic group is bound via an amide linkage to the sugar or sugar alcohol in the component (A), and said component (A) is at a concentration of 0.0001 to 0.1 percent by weight of said composition.

21. A harvested plant freshness-keeping composition comprising at least one surfactant (A) and at least one selected from the group consisting of a sugar (B), a plant hormone (C), an aging inhibitor (D), an aggregating agent for colloidal particles (E) and a germicide, fungicide or preservative (F);
   wherein the component (A) has a hydrophobic group bound via a glycoside linkage to the sugar or sugar alcohol in the component (A), said component (A) is at a concentration of 0.0001 to 0.1 percent by weight of said composition, and component (A) is selected from the group consisting of an alkyl glycoside and an alkyl polyglycoside.

22. The plant freshness-keeping composition of claim 21, wherein said component (A) is an alkyl polyglycoside having 10 to 18 carbon atoms in the hydrophobic group thereof.

23. A harvested plant freshness-keeping composition comprising at least one surfactant (A), wherein said surfactant has a sugar structure or a sugar alcohol structure, and at least one selected from the group consisting of a sugar (B), a plant hormone (C), an aging inhibitor (D), an aggregating agent for colloidal particles (E) and a germicide, fungicide or preservative (F);
   wherein a hydrophobic group is bound via an ester linkage to the sugar or sugar alcohol in the component (A);
   said component (A) is at a concentration of 0.0001 to 0.1 percent by weight of said composition;
   the component (A) is at least one selected from the group consisting of a polyoxyalkylene sorbitan fatty acid ester, a sucrose fatty acid ester, a sorbitol fatty acid ester, a polyoxyalkylene sorbitol fatty acid ester, a polyglycerol, a polyglycerol fatty acid ester, a glycerol fatty acid ester and a polyoxyalkylene glycerol fatty acid ester; and
   component (C) is at least one selected from the group consisting of a natural auxin, synthetic auxin, natural cytokinin, synthetic cytokinin and gibberellin.

24. A harvested plant freshness-keeping composition comprising at least one surfactant (A) and at least one selected from the group consisting of a sugar (B), a plant hormone (C), an aging inhibitor (D), an aggregating agent for colloidal particles (E) and a germicide, fungicide or preservative (F);
   wherein component (A) is at least one selected from the group consisting of a polyoxyalkylene sorbitan fatty acid ester, a sucrose fatty acid ester, a sorbitol fatty acid ester, a polyoxyalkylene sorbitol fatty acid ester, a polyglycerol, a polyglycerol fatty acid ester, a glycerol fatty acid ester and a polyoxyalkylene glycerol fatty acid ester;
   a hydrophobic group is bound via an ester linkage to said component (A), and said component (A) is at a concentration of 0.0001 to 0.1 percent by weight of said composition;
   component (B) is selected from the group consisting of glucose, sucrose and fructose; and
   component (C) is gibberellin.

25. A harvested plant freshness-keeping composition comprising at least one surfactant (A), wherein said surfactant has a sugar structure or a sugar alcohol structure, and at least one selected from the group consisting of a sugar (B), a plant hormone (C), an aging inhibitor (D), an aggregating agent for colloidal particles (E) and a germicide, fungicide or preservative (F);
   wherein either a hydrophobic group is bound via a glycoside linkage to the sugar or sugar alcohol in the component (A) and said component (A) is at a concentration of 0.0001 to 0.1 percent by weight of said composition,
   a hydrophobic group is bound via an ester linkage to the sugar or sugar alcohol in the component (A), or
   a hydrophobic group is bound via an amide linkage to the sugar or sugar alcohol in the component (A);
   the ratio of (A)/(B) by weight is 0.00001 to 2.0; the ratio of (A)/(C) by weight is 0.0002 to 10000; the ratio of (D)/(A) by weight is 0.0002 to 1000; the ratio of (A)/(E) by weight is 0.0002 to 1000; or the ratio of (A)/(F) by weight is 0.00001 to 200;
   wherein said component (C) is at least one selected from the group consisting of indole-3-acetic acid, 2,4-dichlorophenoxyacetic acid, 2,6-dichlorobenzoic acid, naphthalene acetic acid, zeatin, kinetin, 4-benzyl aminobenzimidazole, benzyl adenine and a gibberellin; and
   said composition comprises 0.0001 to 0.5% by weight of component (F).

26. The plant freshness-keeping composition of claim 25, wherein said component (A) is an alkyl polyglycoside having 10 to 18 carbon atoms in the hydrophobic group thereof.

\* \* \* \* \*